United States Patent
Snyder

(10) Patent No.: US 7,927,585 B2
(45) Date of Patent: Apr. 19, 2011

(54) PRODUCTION OF RECOMBINANT AAV VIRIONS

(75) Inventor: Richard O. Snyder, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 582 days.

(21) Appl. No.: 12/020,395

(22) Filed: Jan. 25, 2008

(65) Prior Publication Data

US 2009/0075357 A1 Mar. 19, 2009

Related U.S. Application Data

(63) Continuation of application No. 10/427,432, filed on Apr. 30, 2003, now abandoned.

(60) Provisional application No. 60/377,310, filed on Apr. 30, 2002.

(51) Int. Cl.
*A01N 63/00* (2006.01)
*C12N 15/00* (2006.01)
*C12N 15/74* (2006.01)
*C12N 15/81* (2006.01)

(52) U.S. Cl. .................... 424/93.2; 435/320.1; 435/471; 435/483; 536/23.1; 536/24.1

(58) Field of Classification Search .......................... None
See application file for complete search history.

(56) References Cited

U.S. PATENT DOCUMENTS

| 5,866,404 A | 2/1999 | Bradshaw et al. |
| 6,037,177 A | 3/2000 | Snyder |
| 6,291,214 B1 | 9/2001 | Richards et al. |
| 6,291,246 B1 | 9/2001 | Deleduse et al. |

OTHER PUBLICATIONS

Urabe et al., Insect Cells as a Factory to Produce Adeno-Associated Virus Type 2 Vectors, Human Gene Therapy, 13: pp. 1935-1943, 2002.

Lowin et al., Production of Recombinant Parvovirus B19 VP2-Capsids in *Saccharomyces cerevisiae* for use in Diagnostics, IX Parvovirus Workshop, Bologna, Italy, 2002, abstract.

Wang et al., Adeno-Associated Virus Type 2 DNA Replication in Vivo: Mutation Analyses of the D Sequence in Viral Inverted Terminal Repeat, JVI, 1997, vol. 71, No. 4, pp. 3077-3082.

Walmsley et al., Green Fluorescent Protein as a Reporter for the DNA Damage-Induced RAD54 in *Saccharomyces cerevisiae*, Yeast 1997, vol. 13, pp. 1535-1545.

*Primary Examiner* — Maria Marvich
(74) *Attorney, Agent, or Firm* — Timothy H. Van Dyke; Beusse Wolter Sanks Mora & Maire

(57) ABSTRACT

Stocks of infectious rAAV are generated using yeast strains, bacterial strains, and bacteriophages engineered to express the required AAV proteins and harboring rAAV vector sequences. Stocks of rAAV virions of all serotypes and pseudotypes can be generated in prokaryotic and eukaryotic cells using the methods described herein.

16 Claims, 1 Drawing Sheet

SEQUENCE LISTING

<160> NUMBER OF SEQ ID NOS: 22

<210> SEQ ID NO 1
<211> LENGTH: 17
<212> TYPE: DNA
<213> ORGANISM: Artificial
<220> FEATURE:
<223> OTHER INFORMATION: Synthetic Oligonucleotides

<400> SEQUENCE: 1
tgccggggtt ttacgag                                                    17

<210> SEQ ID NO 2
<211> LENGTH: 19
<212> TYPE: DNA
<213> ORGANISM: Artificial
<220> FEATURE:
<223> OTHER INFORMATION: Synthetic Oligonucleotides

<400> SEQUENCE: 2
ttattgttca aagatgcag                                                  19

<210> SEQ ID NO 3
<211> LENGTH: 19
<212> TYPE: DNA
<213> ORGANISM: Artificial
<220> FEATURE:
<223> OTHER INFORMATION: Synthetic Oligonucleotides

<400> SEQUENCE: 3
gagctggtcg ggtggctcg                                                    19

<210> SEQ ID NO 4
<211> LENGTH: 18
<212> TYPE: DNA
<213> ORGANISM: Artificial
<220> FEATURE:
<223> OTHER INFORMATION: Synthetic Oligonucleotides

<400> SEQUENCE: 4
atggagctgg tcgggtgg                                                     18

<210> SEQ ID NO 5
<211> LENGTH: 44
<212> TYPE: DNA
<213> ORGANISM: Artificial
<220> FEATURE:
<223> OTHER INFORMATION: Synthetic Oligonucleotides

<400> SEQUENCE: 5
tcagagagag tgtcctcgag ccaatctgtc tgcgtagttg atcg                        44

<210> SEQ ID NO 6
<211> LENGTH: 18
<212> TYPE: DNA
<213> ORGANISM: Artificial
<220> FEATURE:
<223> OTHER INFORMATION: Synthetic Oligonucleotides

<400> SEQUENCE: 6
tggctgccga tggttatc                                                     18

<210> SEQ ID NO 7
<211> LENGTH: 19
<212> TYPE: DNA
<213> ORGANISM: Artificial
<220> FEATURE:
<223> OTHER INFORMATION: Synthetic Oligonucleotides

<400> SEQUENCE: 7
atggctgccg atggttatc                                                    19

<210> SEQ ID NO 8
<211> LENGTH: 19
<212> TYPE: DNA
<213> ORGANISM: Artificial
<220> FEATURE:
<223> OTHER INFORMATION: Synthetic Oligonucleotides

<400> SEQUENCE: 8
ttacagatta cgagtcagg                                                    19

<210> SEQ ID NO 9
<211> LENGTH: 21
<212> TYPE: DNA
<213> ORGANISM: Artificial
<220> FEATURE:
<223> OTHER INFORMATION: Synthetic Oligonucleotides

<400> SEQUENCE: 9
tggctccggg aaaaaagagg c                                                 21

<210> SEQ ID NO 10
<211> LENGTH: 22

```
<212> TYPE: DNA
<213> ORGANISM: Artificial
<220> FEATURE:
<223> OTHER INFORMATION: Synthetic Oligonucleotides

<400> SEQUENCE: 10
atggctccgg gaaaaaagag gc                                            22

<210> SEQ ID NO 11
<211> LENGTH: 19
<212> TYPE: DNA
<213> ORGANISM: Artificial
<220> FEATURE:
<223> OTHER INFORMATION: Synthetic Oligonucleotides

<400> SEQUENCE: 11
tggctacagg cagtggcgc                                                19

<210> SEQ ID NO 12
<211> LENGTH: 20
<212> TYPE: DNA
<213> ORGANISM: Artificial
<220> FEATURE:
<223> OTHER INFORMATION: Synthetic Oligonucleotides

<400> SEQUENCE: 12
atggctacag gcagtggcgc                                               20

<210> SEQ ID NO 13
<211> LENGTH: 18
<212> TYPE: DNA
<213> ORGANISM: Artificial
<220> FEATURE:
<223> OTHER INFORMATION: Synthetic Oligonucleotides

<400> SEQUENCE: 13
atgccggggt tttacgag                                                 18

<210> SEQ ID NO 14
<211> LENGTH: 35
<212> TYPE: DNA
<213> ORGANISM: Artificial
<220> FEATURE:
<223> OTHER INFORMATION: Synthetic Oligonucleotides

<400> SEQUENCE: 14
cgggatccaa aaaaatggc tacaggcagt ggcgc                               35

<210> SEQ ID NO 15
<211> LENGTH: 28
<212> TYPE: DNA
<213> ORGANISM: Artificial
<220> FEATURE:
<223> OTHER INFORMATION: Synthetic Oligonucleotides

<400> SEQUENCE: 15
cccaagcttt tacagattac gagtcagg                                      28

<210> SEQ ID NO 16
<211> LENGTH: 41
<212> TYPE: DNA
<213> ORGANISM: Artificial
<220> FEATURE:
<223> OTHER INFORMATION: Synthetic Oligonucleotides

<400> SEQUENCE: 16
ataagaatgc ggccgcaaaa aaaatggagc tggtcgggtg g                       41
```

```
<210> SEQ ID NO 17
<211> LENGTH: 29
<212> TYPE: DNA
<213> ORGANISM: Artificial
<220> FEATURE:
<223> OTHER INFORMATION: Synthetic Oligonucleotides

<400> SEQUENCE: 17
ccttaattaa ttattgttca aagatgcag                                29

<210> SEQ ID NO 18
<211> LENGTH: 34
<212> TYPE: DNA
<213> ORGANISM: Artificial
<220> FEATURE:
<223> OTHER INFORMATION: Synthetic Oligonucleotides

<400> SEQUENCE: 18
cgggatccaa aaaaaatggc tgccgatggt tatc                          34

<210> SEQ ID NO 19
<211> LENGTH: 28
<212> TYPE: DNA
<213> ORGANISM: Artificial
<220> FEATURE:
<223> OTHER INFORMATION: Synthetic Oligonucleotides

<400> SEQUENCE: 19
ctagctagct tacagattac gagtcagg                                 28

<210> SEQ ID NO 20
<211> LENGTH: 45
<212> TYPE: DNA
<213> ORGANISM: Artificial
<220> FEATURE:
<223> OTHER INFORMATION: Synthetic Oligonucleotides

<400> SEQUENCE: 20
ataagaatgc ggccgcaaaa aaaatggctc cgggaaaaaa gaggc              45

<210> SEQ ID NO 21
<211> LENGTH: 29
<212> TYPE: DNA
<213> ORGANISM: Artificial
<220> FEATURE:
<223> OTHER INFORMATION: Synthetic Oligonucleotides

<400> SEQUENCE: 21
ccttaattaa ttacagatta cgagtcagg                                29

<210> SEQ ID NO 22
<211> LENGTH: 41
<212> TYPE: DNA
<213> ORGANISM: Artificial
<220> FEATURE:
<223> OTHER INFORMATION: Synthetic Oligonucleotides

<400> SEQUENCE: 22
ataagaatgc ggccgcaaaa aaaatgccgg ggtttttacga g                 41
```

PRODUCTION OF RECOMBINANT AAV VIRIONS

CROSS REFERENCE TO RELATED APPLICATION

The present application is a continuation application of U.S. application Ser. No. 10/427,432, filed Apr. 30, 2003, now abandoned, the entirety of which is herein incorporated by reference, which claims the benefit of U.S. Provisional Application No. 60/377,310 filed Apr. 30, 2002.

FIELD OF THE INVENTION

The invention relates to the fields of molecular biology, gene therapy, microbiology and virology. More particularly, the invention relates to compositions and methods for producing recombinant AAV virions in non-mammalian cell cultures.

BACKGROUND OF THE INVENTION

Recombinant AAV (rAAV) vectors are increasingly being used for gene transfer and are currently being tested in human gene therapy trials. Conventional methods for producing rAAV are performed using mammalian cell cultures. The difficulties associated with large-scale mammalian cell techniques have hampered production of the large quantities of vectors required for gene therapy applications.

SUMMARY

The invention relates to the development of a new method of producing large quantities of rAAV that do not require mammalian cell cultures. Rather, the invention employs bacterial or yeast cell cultures to generate rAAV stocks. Both bacterial and yeast cultures are significantly easier to work with than mammalian cell cultures. Moreover, the bacteria- or yeast-based methods allow cost-effective production of the large quantities of rAAV required in gene therapy applications.

To produce rAAV in bacterial or yeast cultures, at least two different nucleic acid constructs are introduced into the host cells (i.e, bacteria or yeast). The two different nucleic acids can be (1) a first nucleic acid encoding an exogenous polynucleotide (e.g., a therapeutic gene or a reporter gene) and (2) a second nucleic acid encoding those AAV Cap and Rep proteins necessary for viral replication. The host cells containing the introduced nucleic acids are cultured under conditions that result in the production of rAAV virions.

Accordingly, the invention features a nucleic acid that includes: (A) a polynucleotide interposed between a first AAV inverted terminal repeat and second AAV inverted terminal repeat, or a polynucleotide encoding an AAV Rep and/or Cap protein; (B) a promoter operably linked to the polynucleotide; and (C) a yeast origin of replication. The nucleic acid can be included within a plasmid.

The polynucleotide interposed between a first AAV inverted terminal repeat and second AAV inverted terminal repeat can include a reporter gene such as one that encodes a green fluorescent protein. It can also encode an AAV Rep protein (e.g., Rep 52 or Rep 78) and/or an AAV capsid protein (e.g., VP1, VP2, or VP3). The first and/or second AAV terminal repeat can be an AAV serotype 2 terminal repeat, while the promoter can be a cytomegalovirus promoter. The origin of replication can be 2 micron or an autonomously replicating sequence.

The nucleic acid can further include a selectable marker such as TRP, URA, HIS, LEU, and LYS; a centromere sequence such as CEN6; a transcription termination region (e.g., one from ADH1 or CYC1); and/or a selectable marker such as TRP, URA, HIS, LEU, or LYS.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of virology terms can be found in Granoff and Webster, Encyclopedia of Virology, 2nd edition, Academic Press: San Diego, Calif., 1999; and Tidona and Darai, The Springer Index of Viruses, 1 st edition, Springer-Verlag: New York, 2002. Commonly understood definitions of microbiology can be found in Singleton and Sainsbury, Dictionary of Microbiology and Molecular Biology, 3rd edition, John Wiley & Sons: New York, 2002.

By the term "gene" is meant a nucleic acid molecule that codes for a particular protein, or in certain cases a functional or structural RNA molecule.

As used herein, a "nucleic acid", "nucleic acid molecule", or "polynucleotide" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced by polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

As used herein, "protein" or "polypeptide" are used synonymously to mean any peptide-linked chain of amino acids, regardless of length or post-translational modification, e.g., glycosylation or phosphorylation.

When referring to a nucleic acid molecule or polypeptide, the term "native" refers to a naturally-occurring (e.g., a "wild-type" ("WT")) nucleic acid or polypeptide. A "non-AAV nucleic acid" is a nucleotide sequence not native to AAV.

As used herein, the term "vector" refers to a nucleic acid molecule capable of transporting another nucleic acid to which it has been linked. Vectors capable of directing the expression of genes to which they are operatively linked are referred to herein as "expression vectors."

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

The term "promoter" is used herein to refer to a DNA regulatory sequence to which RNA polymerase binds, initiating transcription of a downstream (3' direction) coding sequence.

As used herein, the terms "rAAV vector" and "recombinant AAV vector" refer to a recombinant AAV-derived nucleic acid.

By the terms "AAV inverted terminal repeats", "AAV terminal repeats", "ITRs", and "TRs" are meant the AAV viral origins of replication. The terms include any fragments or derivatives of a ITR which retain activity of a WT (e.g., full-length) ITR.

Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control. The particular embodiments discussed below are illustrative only and not intended to be limiting.

DETAILED DESCRIPTION

Figure 1:
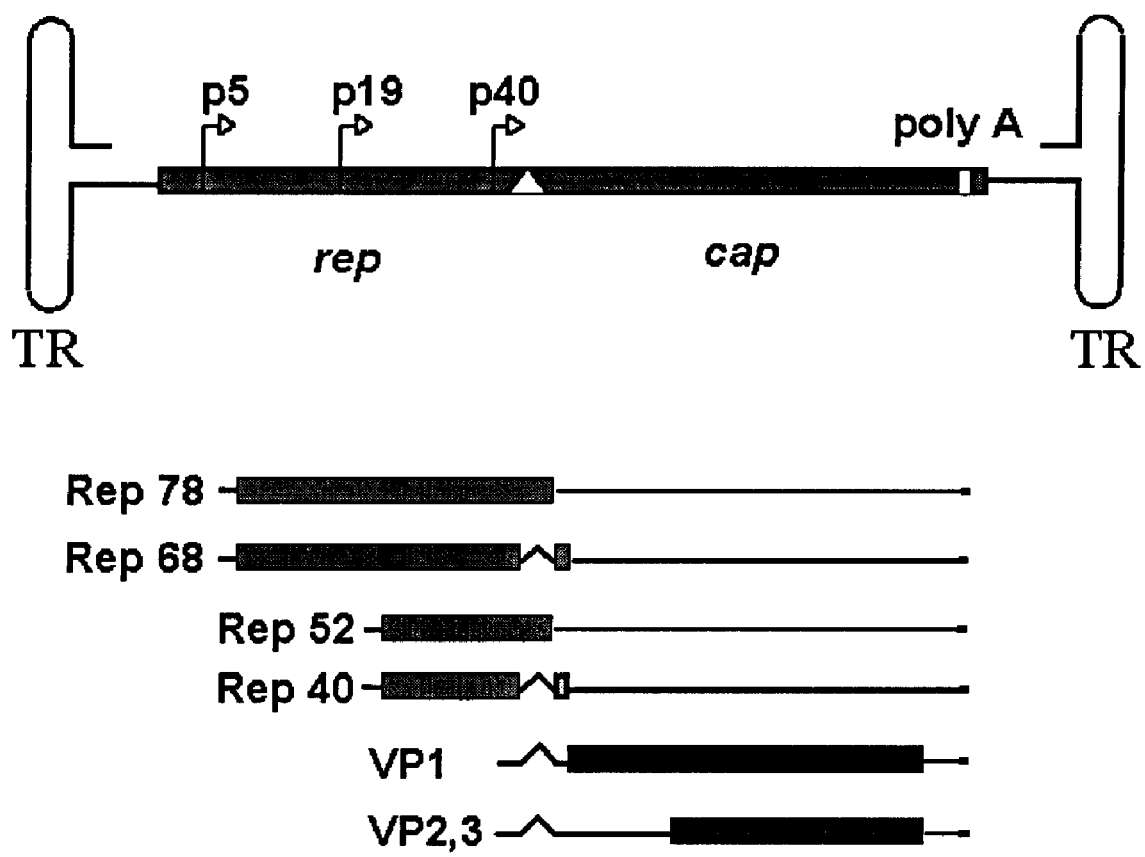
FIG. 1 is a map of the AAV rep and cap open reading frames (ORFs), mRNA, and AAV proteins based on AAV2 sequence deposited with Genbank as accession No. AF043303.

The invention provides methods and compositions for producing rAAV virions in yeast and bacterial cells. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning, 3rd edition, Sambrook and Russell, Cold Spring Harbor Press, 2001; and Current Protocols in Molecular Biology, ed. Ausubel et al., Greene Publishing and Wiley-Interscience, New York, 1992 (with periodic updates). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981.

rAAV Production in Host Cells

In overview, rAAV virions can be produced in large quantities by introducing into host cells both (1) a first nucleic acid construct that encodes an exogenous nucleic acid (i.e., one to be expressed in a cell infected with the virions produced) and (2) a second nucleic acid construct that encodes those AAV Rep and Cap proteins required for viral replication. Both constructs also contain appropriate regulatory sequences that allow them to be efficiently expressed in a particular host cell. In the first nucleic acid construct (e.g., rAAV vector), the exogenous nucleic acid is located between two AAV ITRs that are the minimal cis-acting AAV sequences that direct replication and packaging of an AAV genome as well as an rAAV vector. Typically, the first nucleic acid construct is an rAAV vector. Useful rAAV vectors have one or more of the AAV WT genes deleted in whole or in part, but retain functional flanking ITR sequences.

The first and second nucleic acids may be introduced into host cells by any conventional method, and following introduction the host cells are inoculated into an appropriate medium to start a culture. The culture is incubated under appropriate conditions to allow the host cells to replicate. During this phase, the portion of the first nucleic acid construct containing the two AAV ITRs and exogenous nucleic acid (i.e., rAAV vector) is replicated, resulting in the generation of many rAAV vectors; and the second nucleic acid construct is expressed, resulting in the production of Rep and Cap proteins. Rep proteins (e.g., Rep40, Rep52, Rep68, Rep78) are essential for rAAV vector replication, while the Cap (e.g., VP1, VP2, VP3) proteins are structural proteins that are required for formation of the virion capsid. As a result of expressing capsid proteins in the presence of the replicated vectors, the replicated rAAV vectors are packaged into infectious rAAV virions (i.e., an infectious virus particle containing an rAAV vector). The rAAV virions thus produced are isolated by any of a number of techniques, including chromatography-based and gradient-based purification methods. The construction and purification of rAAV virions has been described. See, e.g., U.S. Pat. Nos. 5,173,414, 5,139,941, 5,863,541, and 5,869,305, 6,057,152, 6,376,237; Rabinowitz et al., J. Virol. 76:791-801, 2002; and Bowles et al., J. Virol. 77:423-432, 2003.

AAV Serotypes rAAV vectors and virions useful in the invention include those derived from a number of AAV serotypes, including 1, 2, 3, 4, 5, 6, and 7. Because of wide construct availability and extensive characterization, preferred rAAV vectors for use in the invention are those derived from serotype 2 (or mutants thereof). A map of the AAV rep and cap ORFs, mRNA, and AAV proteins based on AAV2 sequence (Genbank Accession No. AF043303) is shown in FIG. 1. Construction and use of AAV vectors and AAV proteins of different serotypes are discussed in Chao et al., Mol. Ther. 2:619-623, 2000; Davidson et al., PNAS 97:3428-3432, 2000; Xiao et al., J. Virol. 72:2224-2232, 1998; Halbert et al., J. Virol. 74:1524-1532, 2000; Halbert et al., J. Virol. 75:6615-6624, 2001; and Auricchio et al., Hum. Molec. Genet. 10:3075-3081, 2001.

Nucleic Acid Constructs that Encode An Exogenous Nucleic Acid and Rep and Cap Proteins The first nucleic acid construct described above includes a sequence encoding an exogenous nucleic acid and also contains other sequences that facilitate its expression in a host cell. An exogenous nucleic acid is a nucleic acid that is not native to AAV. The sequence encoding an exogenous nucleic acid is inserted into the construct in such a way that the nucleic acid is expressed. For example, the nucleic acid is placed within a construct (e.g., vector) at a particular location such that: (1) it is between two functional AAV ITRs, (2) it is operatively linked with a promoter and (3) it is placed 5' to a pA tail.

The exogenous nucleic acid can be any nucleic acid that is desired to be included in the rAAV to be produced so long as it does not exceed the number of nucleotides that can be encapsulated within a rAAV virion (i.e., approximately 5 kilobases). Typical examples of such nucleic acids include those that encode a protein or an RNA. Proteins might, for example, be those that exert a therapeutic effect on a diseased cell (e.g., a human or non-human cell). Genes that can be delivered by rAAV to exert a therapeutic effect include alpha-one antitrypsin, clotting factor IX, clotting factor VIII, clotting factor VII, dystrophin, α-, β-, δ-, ε-sarcoglycans, tyrosine hydroxylase, aromatic acid decarboxylase, GTP cyclohydrolaseI, erythropoietin, aspartoacylase (ASPA), Nerve growth factor (NGF), lysosomal beta-glucuronidase (GUSB), insulin, alpha-synuclein, basic fibroblast growth factor (FGF-2), IGF1, alpha-galactosidase A (alpha-gal A), neurotrophin-3, Neuroglobin (Ngb), angoigenic proteins (vascular endothelial growth factor (VEGF165)), anti-angiogenic proteins, and any cytokines, including interferons (IFN-α, IFN-β, IFN-γ), interleukins, GM-CSF (granulocyte-macrophage colony-stimulating factor), M-CSF (macrophage colony-stimulating factor), tumor necrosis factors, growth factors (TGF-β (transforming growth factor-β), IL-10, IL-13, IL-4, and PDGF (platelet-derived growth factor)) or neurotrophic factors CNTF (ciliary Neurotrophic factor), brain-derived neurotrophic factor (BDNF), and GDNF (glial cell line derived neurotrophic factor). Alternatively, proteins might be those that act as reporters or markers of gene expression (e.g., green fluorescent protein (GFP), β-galactosidase, luciferase). RNA may be anti-sense, RNAi, and ribozymes.

The second nucleic acid construct that encodes AAV Rep and Cap proteins also contains sequences that facilitate their expression in a host cell. A nucleic acid encoding a Cap protein is any nucleic acid that encodes at least one functional Cap protein or functional derivative thereof. The AAV cap gene encodes three capsid proteins: VP1, VP2 and VP3, and any one or combination of these three proteins may be expressed by a nucleic acid of the invention. A nucleic acid encoding a Rep protein is any nucleic acid that encodes at least one functional Rep protein or functional derivative thereof. Any one or combination of the four AAV Rep proteins Rep40, Rep52, Rep68, and Rep78, may be expressed by a nucleic acid of the invention. A nucleic acid encoding a Rep and/or Cap protein is inserted into the second nucleic acid construct in such a way that the nucleic acid is expressed. For example, the nucleic acid is placed within a construct (e.g., vector) at a particular location such that: (1) it is operatively linked with a promoter and (2) it is placed 5' to a pA tail.

In some applications, the exogenous nucleic acid and the nucleic acids encoding Rep and Cap are operably linked to one or more expression control sequences that facilitate gene expression in bacteria or yeast. Generally, operably linked nucleic acid sequences are contiguous and, where necessary to join two protein coding regions, in reading frame. Examples of expression control sequences include promoters, insulators, response elements, introns, IRESs, silencers, enhancers, introns, initiation sites, termination signals, and pA tails. Within the invention, any expression control sequence that facilitates gene expression in the host cell (e.g., yeast and bacteria) may be used. Such control elements can include control sequences normally associated with the selected exogenous nucleic acid or nucleic acids encoding Rep and Cap. Alternatively, heterologous control sequences can be employed.

Nucleic Acids For Virion Production in Yeast

To produce the rAAV virions, yeast cells are transformed with nucleic acid constructs (e.g., vectors, plasmids) containing one or more nucleic acids. In a typical method, yeast cells are transformed with a first nucleic acid encoding an exogenous nucleic acid interposed between two AAV ITRs (e.g., rAAV vector) and one or more nucleic acid constructs (e.g., vectors, plasmids) encoding AAV Rep and Cap proteins.

In addition to an exogenous nucleic acid, the first nucleic acid construct further includes a promoter, a selectable marker, and a yeast origin of replication. In a preferred construct, the exogenous nucleic acid is operably linked to a cytomegalovirus promoter and contains a selectable marker (e.g., TRP, LEU2, HIS, URA, LYS). Preferred constructs also contain a yeast origin of replication [e.g., 2 micron, or autonomously replicating sequence (ARS)]. In some applications, the construct includes a centromere sequence (e.g., CEN6) to increase stability of the vector in the yeast cell. Examples of suitable plasmids (e.g., integrating plasmids) for transforming yeast cells with an exogenous nucleic acid interposed between two AAV ITRs include pROS-910 and pROS-911. The construction of these plasmids is described in the Examples section below.

By transforming yeast cells with a construct containing an rAAV vector and one or more nucleic acid constructs encoding Rep and Cap proteins, the rAAV vector is replicated and subsequently encapsulated by rAAV virions within the yeast cell. A typical nucleic acid construct encoding at least one Cap protein (e.g., VP1, VP2, VP3) and at least one Rep protein (e.g., Rep52, Rep78) contains several components. These components include: a nucleic acid encoding at least one AAV Rep protein, a nucleic acid encoding at least one AAV Cap protein, at least one yeast-specific transcription termination region, at least one promoter that functions in yeast, a selectable marker, and a yeast origin of replication. The individual AAV Rep (78, 68, 52, and 40) and Cap (VP1, VP2, VP3) genes can be expressed separately or together in a polycistronic arrangement in yeast cells. To express the genes in a polycistronic arrangement, the genes are linked and inserted into a suitable expression vector.

In a preferred method for producing rAAV virions in yeast cells, a first nucleotide sequence encoding Rep52 and VP3 and a second nucleotide sequence encoding VP1, VP2, and Rep78 are used to transform yeast cells. For example, plasmid pROS-921 contains a nucleotide sequence encoding VP3 operatively linked to both a GAL1 promoter and a CYC1 transcription termination region, a nucleotide sequence encoding Rep52 operatively linked to both a GAL10 promoter and a ADH1 transcription termination region, a LEU2 selectable marker, and a 2 micron origin of replication. This plasmid can be used in conjunction with pROS-914 which contains a nucleotide sequence encoding VP1 operatively linked to both a GAL1 promoter and a CYC1 transcription termination region, a nucleotide sequence encoding VP2 operatively linked to both a GAL10 promoter and a ADH1 transcription termination region, a nucleotide sequence encoding Rep78 operatively linked to both a GAL10 promoter and a ADH1 transcription termination region, an ARS4 sequence, a CEN6 sequence, and a TRP1 selectable marker.

To achieve appropriate levels of AAV (e.g, Rep and Cap) proteins in yeast cells, any of a number of promoters suitable for use in yeast cells may be employed. Examples of yeast-specific promoters include GAL1, GAL10, CYC1, and ADH. Constitutive promoters of different strengths can be used to express the different AAV proteins in yeast cells. Examples of useful constitutive promoters include the GAP promoter found in Invitrogen's *P. pastoris* expression system (Invitrogen, Carlsbad, Calif.), the TEF1 promoter found in the *P. methanolica, P. pastoris*, and *S. cerevisiae* systems, and the KEX2 and TDH promoters found in *S. cerevisiae* systems. Alternatively, inducible promoters may be used to express protein in yeast cells. Examples of inducible (e.g., regulated) promoters include (1) the AOX1 methanol-regulated promoter found in Invitrogen's *P. pastoris* expression system (Invitrogen, Carlsbad, Calif.), (2) the GAL1 galactose-regulated promoter found in pYC2-E or pYES2.1E *S. cerevisiae* expression system (Invitrogen), (3) the nmt promoters regulated by thiamine found in Invitrogen's *S. pombe* SpECTRA expression system (Invitrogen, Carlsbad, Calif.), and (4) the AUG1 methanol regulated promoter found in Invitrogen's *P. methanolica* expression system.

Exogenous nucleic acids and rAAV nucleic acid sequences (e.g., ITRs, rep, cap) used in the invention can be incorporated in yeast using a variety of constructs (e.g., vectors, plasmids) and can reside in the yeast chromosome, yeast artificial chromosomes (YACs), or on ARS plasmids as well as other standard yeast cloning plasmids. A number of suitable plasmids are described herein. For example, plasmid TR-UF-5 (Klein et al., Exp Neurol. 150:183, 1998) contains an rAAV vector and was cloned into yeast plasmids pRS403, 404, 405, and 406, which are examples of chromosomal integrating plasmids. Examples of low copy episomal plasmids that can be used in methods of the invention include plasmids pRS413, 414, 415, and 416. Plasmids pRS423, 424, 425, and 426 are examples of high copy episomal plasmids that can also be used. Each member of these series have different selectable markers (ATCC #87538). pYAC4 is a yeast artificial chromosome (Sigma, St. Louis, Mo.; see Sambrook and Russell, supra.) that may be useful in methods of the invention.

Large-scale culturing of yeast and expression of proteins may be conducted using any suitable yeast culturing technique. Such techniques are well known in the art and include those described in Burgers, Methods 18:349, 1999. According to this method, culturing of yeast is performed under galactose control. Yeast cells are grown for 2-3 days in 100 ml of selective SCGL medium. The cells are grown at 30° C. until saturation and inoculated into 1200 ml of the same medium in a 4-liter flask and grown overnight. An equal volume of YPGLA is then added to the overnight culture. The culture is equally divided between two flasks and grown at 30° C. for 3 h. Solid galactose (26 g per flask, 2% final) is then added to the cultures and shaking continued for another 4 h. The cells are harvested by centrifugation at 1500 g for 5 min at 4° C. The yeast is stored frozen at −70° C.

To purify rAAV virions from cultured yeast cells, a number of methods may be employed. In one example of such a method, the yeast cells are resuspended in lysis buffer (20 mM Tris-Cl pH=8, 150 mM NaCl, 0.5% deoxycholate), and lysed using glass beads. The lysate is treated with Benzonase (Sigma, St. Louis, Mo.) and centrifuged at 4000 g and the supernatant is chromatographed on Streamline HE column (Pharmacia), Phenyl Sepharose, and POROS HE (Potter et al., Methods Enzymol 346:413-30, 2002).

To assess virion performance, the purified rAAV virions are used to infect 293 cells in culture or are injected into mouse skeletal muscle to assess their infectivity by scoring for cells expressing GFP.

Optimization of Rep and Cap Expression in Yeast

To achieve appropriate levels of the AAV proteins in yeast several strategies can be incorporated. For example, AAV rep and cap ORF codons can be optimized for expression in yeast (See Outchkourov et al., Protein Expr Purif. 24:18-24, 2002; and Kanaya et al., J Mol Evol 53:290-8, 2001). As another example, the protein levels can be controlled at the level of translation using a variety of methods. Such methods include inefficient translational start codons and context, suppressor tRNAs, antisense, mRNA destabilization, and ribozymes. Non-AUG initiation codons (UUG, AUU, AUA, GUG) are utilized at lowered efficiency (Broach, Pringle, Jones, Eds. Cold Spring Harbor Laboratory Press. Vol 1 p. 627-735. 1991). See Miyasaka Yeast 15:633-7, 1999, for initiation codon context. See Romanos et al., (Yeast 8:423, 1992) for a review of foreign gene expression in yeast.

Additionally, the protein levels can be controlled post-translationally using methods including phosphorylation, ubiquitination, and proteases. See Finley, D. The yeast ubiquitin system. In Molecular and cellular biology of Yeast *Saccharomyces*. Jones, Pringle, Broach, Eds. Cold Spring Harbor Laboratory Press. Vol2 p. 539-81. 1992

To further optimize rAAV production, the yeast strains can be recombination deficient to reduce or eliminate the generation of replication-competent rAAV (rcAAV) contamination. rcAAV can be generated by the event of recombination between rAAV vector sequences and AAV Rep and Cap sequences. Several yeast mutations have been identified with reduced recombination efficiency. See Petes et al., Recombination in Yeast. In Molecular and cellular biology of Yeast *Saccharomyces*. Broach, Pringle, Jones, Eds. Cold Spring Harbor Laboratory Press. Vol 1 p. 407-521. 1991.

Bacteria-Specific Nucleic Acids

By introducing into bacterial cells a nucleic acid construct encoding an rAAV vector containing an exogenous nucleic acid and a nucleic acid construct encoding Rep and Cap proteins, the rAAV vector is replicated and subsequently encapsulated by rAAV virions within the bacterial cell. Bacterial cells of the invention include any bacteria that can be used to express exogenous nucleic acids. For example, *E. coli* are suitable for use within the invention. Methods of using *E. coli* for exogenous nucleic acid expression are widely known in the art and are described in Current Protocols in Protein Science, Coligan et al., John Wiley & Sons, New York; 1995-2001. Other bacterial cells of the invention include bacteria belonging to the genera *Mycobacterium, Corynebacterium, Nocardia,* and *Streptomyces*. Methods involving heterologous protein expression in *Mycobacterium, Corynebacterium, Nocardia* and *Streptomyces* are known and can be found in Connel, N. D. Curr. Opin. Biotechnol. 12:446, 2001.

As one example, to produce the rAAV virions, bacterial cells are transformed with the two nucleic acid constructs described above containing expression control sequences that enable replication and expression of the nucleic acids in the bacterial cells. The individual AAV rep (78, 68, 52, and 40) and cap (VP1, VP2, VP3) genes can be expressed separately or together in a polycistronic arrangement in bacterial cells. To express the genes in a polycistronic arrangement, the genes are linked and inserted into a suitable expression vector. Typically, nucleic acid constructs for expression in bacterial cells include a bacterial origin of replication, a promoter, and a selectable marker (e.g., ampicillin, kanamycin, tetracycline).

Preferred nucleic acids of the invention (e.g., nucleic acids encoding Rep and Cap) are operably linked to a promoter that facilitates gene expression in bacterial cells. Constitutive promoters of different strengths, as well as inducible promoters can be used to express the polynucleotides in bacterial cells. Examples of inducible (e.g., regulated) promoters include (1) the arabinose-regulated promoter found in Invitrogen's pBAD expression system, (2) the T7 promoter found in pET-Blue-1 (Novagen, Madison, Wis.) or pTWIN (New England BioLabs, Beverly, Mass.) activated by T7 RNA polymerase which is induced by isopropyl β-D-1-thiogalactopyranoside (IPTG) in BL21 bacterial cells, (3) trc promoter in combination with lacI/O found in Invitrogen's trc expression system is induced by IPTG, (4) PL promoter found in Invitrogen's pLEX plasmids that is controlled by tryptophan, and (5) T5 promoter in combination with lacI/O in Qiagen's pQE vectors (Quiagen, Valencia, Calif.).

Exogenous nucleic acids and rAAV nucleic acid sequences (e.g., ITRs, rep, cap) used in methods of the invention can be incorporated in bacteria using a variety of constructs (e.g., vectors, plasmids). A number of suitable plasmids are known. For example, a plasmid containing rAAV vector sequence pTR-UF-5 (Klein et al., Exp Neurol. 150:183, 1998) is propagated in $E. coli$ under Amp selection. To produce rAAV vector, plasmid pTR-UF-5 is modified by exchanging the $Amp^r$ gene for the $Kan^r$ gene. pTR-UF-5 is digested with restriction enzyme PciI and partially digested with DraIII, and the AAV expression cassette is isolated. pShuttle-CMV (Stratagene, La Jolla, Calif.) is digested with PciI and DraIII and the $Kan^r$ ORF and pBR322 origin of replication is isolated and ligated to the AAV expression cassette to generate pTR-UF-5-$Kan^r$ that is propagated in PMC-107 $E. coli$ (Raman et al., Anal Biochem 245:242, 1997) under Kan selection. To confirm integrity of the cloned sequence, plasmid DNA is isolated and sequenced. Further examples of standard cloning vectors include F-factor, P1, pUC, pBR, and more particularly, P1 cloning vector pAD10SacBII.

In some applications, rAAV vector sequences reside within the bacterial chromosome or within bacterial artificial chromosomes (BACs). Both chromosomes can be used to clone the AAV sequences for maintenance in bacteria (see Sambrook and Russell, supra). An example of a suitable BAC is pBeloBAC11 (New England BioLabs, Beverly, Mass.). For integration into the $E. coli$ bacterial chromosome, see Martinez-Morales et al., J. Bacteriol. 181:7143, 1999.

Bacterial cells harboring the nucleic acid constructs may be cultured using any culturing conditions that allow for replication and growth of the bacterial cells. In one example of culturing bacterial cells, at least one bacterial cell is grown in a shaker flask at 30° C. at 200 rpm and induced with IPTG and tryptophan, followed by an incubation at 37° C. for 16 hours. Samples of the cell culture are taken every 4 hours. Whole cell lysates are made and separated on a 10% sodium dodecyl sulfate polyacrylamide gel electrophoresis (SDS-PAGE) gel, transferred to nitrocellulose and probed with antibodies to: (1) a polypeptide expressed by the exogenous nucleic acid, (3) Rep, or (4) Cap. Detection is carried out using a secondary antibody (e.g., anti-mouse horse radish peroxidase (HRP)-conjugated monoclonal antibody) and a detection reagent (e.g., Pierce Supersignal reagent (Pierce, Rockford, Ill.). In addition, replication of the rAAV vector is evaluated by isolating vector DNA by the method of Hirt (J Mol. Biol. 26:365, 1967) and separating on a 1% agarose gel stained with ethidium bromide. Infectious virions are detected by infecting 293 tissue culture cells with bacterial lysates treated with chloroform and scoring for GFP expression.

To purify rAAV virions from bacterial cells, any suitable method may be used. An example of a typical method includes harvesting of the bacteria by centrifugation, resuspending in lysis buffer (20 mM Tris-Cl pH=8, 150 mM NaCl, 0.5% deoxychloate), and lysing using a French press and treating with Benzonase (Sigma, St. Louis, Mo.). The lysate is centrifuged at 4000 g and the supernatant is chromatographed on Streamline HE column (Pharmacia), Phenyl Sepharose, and POROS HE (Potter et al., Methods Enzymol. 346:413-30, 2002). To assess virion performance, the purified rAAV vectors are assayed as described above for virions produced in yeast cells.

Optimization of Rep and Cap Expression in Bacteria

To achieve appropriate levels of the AAV proteins in bacteria, several strategies can be employed. Appropriate levels of the AAV proteins are required to generate high yields of infectious rAAV virions. (Li et al., J. Virol. 71: 5236-5243, 1997). The optimum protein levels in mammalian vector production systems is higher levels of Rep 52/40 protein compared to Rep 78/68, and a capsid protein ratio of approximately 1:1:10 or 1:1:20 of VP1, 2, and 3.

In one method of achieving appropriate levels of AAV protein expression, AAV rep and cap ORF codons can be optimized for expression in bacteria (See Sambrook and Russell, supra; and Gouy and Gautier, Nucleic Acids Res 10:7055, 1982). As another example, protein levels can be controlled at the level of translation using any of a number of methods. Such methods include inefficient translational start codons and context, suppressor tRNAs, antisense, mRNA destabilization, antibiotics, and ribozymes. Inefficient translation initiation can be achieved by separating the prokaryotic ribosome binding site (or Shine-Dalgamo sequence) from the AUG initiator codon more than the optimal 5-13 basepairs (see Kozak, Microbiol. Rev. 47: 1, 1983; and Gold Ann. Rev. Biochem. 57:199, 1988). Alternative translation initiation codons can be used such as GUG or UUG which are less prevalent (See Genes VII, Lewin, p.147, Oxford University Press, 2000). Antibiotics can be used to decrease protein expression (See Sambrook and Russell, supra). Lastly, translation reinitiation efficiencies can be varied for cistrons expressed from polycistronic mRNA (see Andre, et al., FEBS Letters 468:73. 2000).

Additionally, the AAV sequences (e.g., ITRs, rep, cap) can be placed on separate plasmids or BACs, and the gene, plasmid, or BAC copy number can be varied. The plasmid copy number of pMB1 (pUC plasmids)-based replicons is >100, colE1 (pBR322) based replicons is 15-20, and pSC101-based replicons is ~5. Plasmids having different replicons (members of different incompatibility groups) can be maintained within the same bacterium. Different plasmids within the same incompatibility group may coexist, provided they are under different antibiotic selection (e.g., Amp, Kan, Cam, Tet). Plasmid copy number can be controlled in $E. coli$ strains such as ABLE C or ABLE K (Stratagene, La Jolla, Calif.). See Sambrook and Russell, supra.

To further optimize production of rAAV virions, the bacterial strains used can be recombination deficient to reduce or eliminate the generation of rcAAV contamination. Stratagene's SURE cells (Stratagene, La Jolla, Calif.) are an example of such a strain. Examples of other strains that can be used in the invention include strains that are engineered to reduce protein aggregation by expressing chaperones. Methods of use of such strains are described in Mogk et al., EMBO J. 18:6934, 1999.

Production of rAAV Virions in Bacteriophages

The invention encompasses production of rAAV virions in bacteriophages engineered to contain the first and second nucleic acid constructs described above. Different bacteriophages can be used such as lambda phage or M13. rep, cap, and rAAV vector sequences (including exogenous nucleic acids) can reside in single or separate bacteriophages. Methods involving bacteriophages are described in Sambrook and Russell, supra.

The nucleic acid constructs can be inserted into bacteriophages using any suitable method. For example, each individual rep or cap coding region can be inserted into the EcoRV cloning site in pETBlue-1, AccepTor (Novagen, Madison, Wis.). The AAV coding sequence and flanking regulatory sequences are isolated using AflIII and BspEI, then ligated to EcoRI phage lambda arms of λgt10 or Lambda FixII (Stratagene, La Jolla, Calif.). The AAV coding sequences are also directly ligated to phage lambda arms EcoRI cloning site in λgt11 or λZAP expression vectors (Stratagene, La Jolla, Calif.) for utilization of the lac promoter. See Sambrook and Russell, supra.

To optimize production of rAAV virions in bacteria, the engineered bacteriophage can have a WT growth phenotype, conditional growth phenotype (such as temperature-sensitive or cold-sensitive), or have a mutation that is complemented by an appropriate bacterial strain or helper phage. The phage can induce cell lysis to release the rAAV virions, or phage mutants can be used which do not lyse (lysogenic) and result in intracellular rAAV virions.

Bacteriophage-based rAAV virion production methods may also incorporate bacterial strains harboring proviral rAAV vector sequences either in the bacterial chromosome, BACs, or on plasmids. These bacteria can be infected with bacteriophages harboring exogenous nucleic acids and/or nucleic acids encoding proteins (e.g., Rep, Cap) required for producing rAAV virions. In one method of the invention, plasmid pTR-UF-5 (Klein et al., Exp Neurol. 150:183, 1998) contains rAAV vector sequence and is propagated in $E.$ $coli$ BL21 under Amp selection. $E.$ $coli$ containing pTR-UF-5 can be infected with lambda phages expressing Rep and Cap proteins under control of the T7 promoter. Also within the invention are bacteria different from $E.$ $coli$ that are capable of infection by bacteriophage and heterologous protein expression. See Current Protocols in Protein Science, Coligan et al., John Wiley & Sons, New York; 1995-2001; and Connel, N. D. Curr. Opin. Biotechnol. 12:446, 2001.

rAAV Mutants

The invention also relates to the production of rAAV virions that have mutations within the virion capsid. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., (J. Virol. 74:8635-45, 2000). Pseudotyped rAAV virions, in which an rAAV vector derived from a particular serotype is encapsidated within a capsid containing proteins of another serotype, may also be used in methods of the invention. Techniques involving pseudotyping of AAV virions are known in the art and are described in Halbert et al., (J. Virol. 74:1524-1532, 2000); and Auricchio et al., (Hum. Molec. Genet. 10:3075-3081, 2001). Other rAAV virions that can be used in methods of the invention include those capsid hybrids that are generated by molecular breeding of viruses as well as by exon shuffling. See Soong et al., Nat. Genet. 25:436-439, 2000; and Kolman and Stemmer Nat. Biotechnol. 19:423-428, 2001.

EXAMPLES

The present invention is further illustrated by the following specific examples. The examples are provided for illustration only and are not to be construed as limiting the scope or content of the invention in any way.

Example 1

Cloning of AAV Sequences into Plasmids

Vector Plasmid. The rAAV plasmid pTR-UF-5 (Klein et al., Exp Neurol. 150:183, 1998) is modified by exchanging the Amp$^r$ gene for the Kan$^r$ gene. pTR-UF-5 is digested with restriction enzyme PciI and partially digested with DraIII, and the AAV expression cassette is isolated. pShuttle-CMV (Stratagene, La Jolla, Calif.) is digested with PciI and DraIII and the Kan$^r$ ORF and pBR322 origin of replication is isolated and ligated to the AAV expression cassette to generate pTR-UF-5-Kan$^r$ that is propagated in PMC-107 $E.$ $coli$ (Raman et al., Anal Biochem 245:242, 1997) under Kan selection. Plasmid DNA is isolated and sequenced.

Polycistronic AAV Rep expressing plasmid. For expression of AAV2 Rep78, the AAV Rep 78 coding region is generated from pSM620 (Samulski Proc Natl Acad Sci U S A 79(6):2077-81, 1982) by PCR using VENT DNA polymerase (New England BioLabs, Beverly, Mass.) and oligonucleotide primers with the following sequences: 5' TGCCGGGGTTT-TACGAG 3' (SEQ ID NO:1) and 5'TTATTGTTCAAAGAT-GCAG 3' (SEQ ID NO:2). For expression of AAV2 Rep40, the AAV Rep 40 coding region is generated from pSM620 by PCR using VENT DNA polymerase (New England BioLabs, Beverly, Mass.) and oligonucleotide primers with the following sequences: 5'GAGCTGGTCGGGTGGCTCG 3' (SEQ ID NO:3) (or 5' ATGGAGCTGGTCGGGTGG 3', SEQ ID NO:4) and 5' TCAGAGAGAGTGTCCTCGAGCCAATCT-GTCTGCGTAGTTGATCG 3' (SEQ ID NO:5). The Rep 40 and Rep 78 PCR products are ligated together in the orientation where the 3' end of the Rep40 gene is ligated directly to the 5'end of the Rep78 gene. This provides a translation reinitiation sequence TG$\overline{ATG}$ and allows expression of Rep78 (the downstram $\overline{cistron}$) in addition to Rep40. pTrcHis2 (Invitrogen, Carlsbad, Calif.) is digested with NcoI and PmeI (to remove the multiple cloning site, myc epitope and His tag), and the NcoI site is filled in blunt to recreate the ATG translation initiation codon. The Rep40-Rep78 ligation product is cloned into the blunt ended pTrcHis2 vector so the ATG from pTrcHis2 initiates translation of the Rep40 gene. This plasmid is called pROS 802. Expression is under the control of the trc promoter and the plasmid is propagated under Amp selection in DH5-alpha $E.$ $coli$. Transformants are screened for AAV Rep expression using anti-Rep (295.5, Progen, Brisbane, Australia) antibody after induction with IPTG. Plasmid DNA is isolated and sequenced.

Polycistronic AAV Cap Plasmid. For expression of AAV2 VP1, the AAV VP1 coding region is generated from pSM620 by PCR using VENT DNA polymerase and oligonucleotide primers with the following sequences: 5' TGGCTGC-CGATGGTTATC 3' (SEQ ID NO:6) (or 5' ATGGCTGC-CGATGGTTATC 3', SEQ ID NO:7) and 5'TTACAGATTAC-GAGTCAGG 3' (SEQ ID NO:8). For expression of AAV2 VP2, the AAV VP2 coding region is generated from pSM620 by PCR using VENT DNA polymerase and oligonucleotide primers with the following sequences: 5' TGGCTCCGG-GAAAAAAGA GGC 3' (SEQ ID NO:9) (or 5' ATGGCTC-CGGGAAAAAAGAGGC 3', SEQ ID NO:10) and 5' TTA-CAGATTACGAGTCAGG 3' (SEQ ID NO:8). For expression of AAV2 VP3, the AAV VP3 coding region is generated from pSM620 by PCR using VENT DNA polymerase and oligonucleotide primers with the following sequences: 5' TGGC-TACAGGCAGTGGC GC 3' (SEQ ID NO:11) (or 5' ATGGC-TACAGGCAGTGGCGC 3', SEQ ID NO:12) and 5' TTACAGATTACGAGTCAGG 3' (SEQ ID NO:8).

The VP2, VP3, and VP1 PCR products are ligated together in the orientation where the 3' end of the VP2 gene is ligated directly to the 5'end of the VP3 gene, and the 3' end of the VP3 gene is ligated directly to the 5' end of the VP1 gene. This provides a translation reinitiation sequence TAATG between the VP2 and VP3 genes and the VP3 and V$\overline{P1}$ genes that allows expression of VP3 and VP1 (the downstream cistrons)

in addition to VP2. pLEX (Invitrogen, Carlsbad, Calif.) is digested with NdeI and SalI (to remove the multiple cloning site), and the NdeI and SalI sites are filled in blunt. The ATG translation initiation codon for VP2 is recreated when the VP2,3,1 ligation product is inserted with the 5' end of the VP2 gene ligated to the blunt NdeI site. This plasmid is called pROS 804. Expression is under the control of the PL promoter and the plasmid is transformed into bacterial strain G1724 (Invitrogen, Carlsbad, Calif.) at 30° C. under Amp selection. Transformants are screened for AAV capsid expression using anti-Cap (B1, Progen, Brisbane, Australia) antibody after induction with tryptophan and incubation at 37° C. Plasmid DNA is isolated and sequenced.

In applications where Rep52 and Rep68 expression is desired, these sequences can be cloned by the following methods. For expression of AAV2 Rep68, the AAV Rep 68 coding region is generated from pSM620 by PCR using oligonucleotide primers with the following sequences: 5' ATGCCGGGGTTTTACGAG 3' (SEQ ID NO:13) and 5' TCAGAGAGAGTGTCCTCGAGCCAATCT-GTCTGCGTAGTTGATCG 3' (SEQ ID NO:5). For expression of AAV2 Rep52, the AAV Rep 52 coding region is generated from pSM620 by PCR using oligonucleotide primers with the following sequences: 5' ATGGAGCTG-GTCGGGTGG 3' (SEQ ID NO:4) and 5' TTATTGTTCAAA-GATGCAG 3' (SEQ ID NO:2).

Example 2 rAAV Virion Production

Bacterial Strains. The rAAV vector plasmid pTR-UF-5-Kan$^r$ is transformed into bacterial strain G1724 and selected using Kan; the subsequent strain is called EcVector. The AAV Rep plasmid pROS-802 expressing AAV Rep 78 and 40 proteins, and the AAV Cap plasmid pROS-804 expressing AAV VP1, 2, and 3 are transformed into the EcVector strain and selected using Amp and Kan to create strain EcVRC.

rAAV Virion Production. To optimize rAAV vector production, strain EcVRC is grown in a shaker flask at 30° C. at 200 rpm and induced with IPTG, tryptophan, and incubated at 37° C. for 16 hours. Samples of the cell culture are taken every 4 hours. Whole cell lysates are made and separated on a 10% SDS-PAGE gel, transferred to nitrocellulose and probed with anti-Rep (295.5, Progen, Brisbane, Australia) and anti-Cap (B1, Progen, Brisbane, Australia) antibodies. Detection is carried out using anti-mouse HRP-conjugated monoclonal antibody and Pierce Supersignal reagent (Pierce, Rockford, Ill.). In addition, replication of the rAAV-UF-5 vector genome is evaluated by isolating vector DNA by the method of Hirt (J Mol. Biol. 26:365, 1967) and separating on a 1% agarose gel stained with ethidium bromide. Infectious virions are detected by infecting 293 tissue culture cells with bacterial lysates treated with chloroform and scoring for GFP expression.

rAAV Virion Purification. Bacteria is harvested by centrifugation, resuspended in lysis buffer (20 mM Tris-Cl pH=8, 150 mM NaCl, 0.5% deoxychloate), and lysed using a French press and treated with Benzonase (Sigma, St. Louis, Mo.). The lysate is centrifuged at 4000 g and the supernatant is chromatographed on Streamline HE column (Pharmacia), Phenyl Sepharose, and POROS HE (Potter et al., Methods Enzymol. 346:413-30, 2002).

rAAV Virion Performance. The purified rAAV vectors are used to infect 293 cells in culture or injecting into skeletal muscle to assess their infectivity by scoring for cells expressing GFP.

Example 3

Cloning of AAV Sequences into Plasmids for use in Bacteriophage

Vector Plasmid. The rAAV plasmid pTR-UF-5 (Klein et al., Exp Neurol. 150:183, 1998) is modified by exchanging the Amp$^r$ gene for the Kan$^r$ gene. pTR-UF-5 is digested with restriction enzyme PciI and partially digested with DraIII, and the AAV expression cassette is isolated. pShuttle-CMV (Stratagene, La Jolla, Calif.) is digested with PciI and DraIII and the Kan$^r$ ORF and pBR322 origin of replication is isolated and ligated to the AAV expression cassette to generate pTR-UF-5-Kan$^r$ that is propagated in PMC-107 E. coli under Kan selection (Raman et al., Anal Biochem 245:242, 1997). Plasmid DNA is isolated and sequenced.

Polycistronic AAV Rep expressing plasmid. The coding regions of Rep40 and Rep78 are generated using the same methodology and oligonucleotides as those described above for expression in bacteria.

Polycistronic AAV Cap Phage. A VP2,3,1 ligation product is generated using the same methodology and oligonucleotides as those described above for expression in bacteria. The VP2,3,1 ligation product is then inserted into the EcoRV cloning site in pETBlue-1 Blunt (Novagen, Madison, Wis.) with the 5' end of the VP2 gene ligated proximal to the T7 promoter. This plasmid is called pROS-806. Expression is under the control of the T7 promoter and the plasmid is transformed into bacterial strain DH5-alpha under Amp selection. Plasmid DNA is isolated and sequenced. Plasmid pROS-806 is transformed into bacterial strain BL21-AI (Invitrogen, Carlsbad, Calif.) under Amp selection. Transformants are screened for AAV capsid expression using anti-Cap (B1, Progen, Brisbane, Australia) antibody after induction with arabinose. The AAV cap coding sequence and flanking regulatory sequences are isolated by digestion of pROS-806 with AflIII and BspEI and ligated to EcoRI phage lambda arms of λgt10 (Stratagene, La Jolla, Calif.) using AflIII-EcoRI and BspEI-EcoRI linkers to create lambda-Cap. The ligation mixture is electroporated into C600hflA150 bacteria and the cells are mixed with C600hflA150 bacterial cells grown in maltose and MgSO$_4$, and plated. Plaques are picked and amplified by infecting C600hflA150 bacterial cells grown in maltose and MgSO$_4$. Bacterial strain BL21-AI (Invitrogen, Carlsbad, Calif.) is grown in maltose and MgSO$_4$, induced with arabinose, and infected with lambda-cap clones to screen for AAV capsid expression using anti-Cap (B1, Progen, Brisbane, Australia) antibody.

Example 4 rAAV Virion Production in Bacteria Infected with Bacteriophage

Bacterial Strains. The rAAV vector plasmid pTR-UF-5-Kan$^r$ is transformed into bacterial strain BL21-AI and selected using Kan; the subsequent strain is called BL21 Vector. The AAV Rep plasmid pROS-802 expressing AAV Rep 78 and 40 proteins is transformed into the BL21 Vector strain and selected using Amp and Kan to create strain BL21RepVec. Transformants are screened for AAV Rep expression using anti-Rep (295.5, Progen, Brisbane, Australia) antibody after induction with IPTG.

rAAV Virion Production. To optimize rAAV vector production, strain BL21RepVec is grown in a shaker flask at 200 rpm in maltose and MgSO$_4$, induced with IPTG and arabinose, infected with lambda-Cap, and incubated at 37° C. for 16 hours. Samples of the cell culture are taken every 4 hours. Whole cell lysates are made and separated on a 10% SDS-PAGE gel, transferred to nitrocellulose and probed with anti- Rep (295.5, Progen, Brisbane, Australia) and anti-Cap (B1, Progen, Brisbane, Australia) antibodies. Detection is carried out using anti-mouse HRP conjugated monoclonal antibody and Pierce Supersignal reagent (Pierce, Rockford, Ill.). In addition, replication of the rAAV-UF-5 vector genome is evaluated by isolating vector DNA by the method of Hirt (J. Mol. Biol. 26:365, 1967) and separating on a 1% agarose gel stained with ethidium bromide. Infectious rAAV virions are detected by infecting 293 tissue culture cells with bacterial lysates and culture media following chloroform extraction and scoring for GFP expression.

rAAV Virion Purification. Bacteria is harvested by centrifugation and resuspended in lysis buffer (20 mM Tris-Cl pH=8, 150 mM NaCl, 0.5% deoxychloate). The culture media is harvested separately and adjusted to 20 mM Tris-Cl pH=8, 150 mM NaCl, 0.5% deoxychloate. The lysate is treated with Benzonase (Sigma, St. Louis, Mo.) and is centrifuged at 4000 g and the supernatants are chromatographed on Streamline HE column (Pharmacia), Phenyl Sepharose, and POROS HE (Potter et al., Methods Enzymol 346:413-30, 2002).

rAAV Virion Performance. The purified rAAV vectors are used to infect 293 cells in culture to assess their infectivity by scoring for cells expressing GFP.

Example 5

Cloning AAV Sequences into Plasmids for Use in Yeast

Vector Plasmids: A rAAV plasmid pTR-UF-5 (Klein, R L, et al., Exp Neurol. 150:183, 1998) was partially digested with ScaI and NaeI, and the ITR containing AAV vector fragment (position 6046-4975) was isolated. pESC-URA (Stratagene, La Jolla, Calif.) was partially digested in ScaI and NaeI and the fragment containing the high copy 2-micron origin and URA3 elements (position 4786-1679) was isolated. The pESC-URA fragment (position 4786-1679) was ligated to the pTR-UF-5 ScaI-NaeI AAV vector fragment using the Quick Ligation™ Kit (New England BioLabs, Beverly, Mass.) to create pROS-910 (selections: URA for yeast and Amp for bacteria) and sequenced. The plasmid is propagated in the SURE® bacterial strain under Amp selection.

The rAAV plasmid pTR-UF-5 (Klein et al., Exp Neurol. 150:183, 1998) is digested with AseI (position 3432) and PvuI (position 6219) and blunt ended with Klenow. The AAV vector fragment (position 6219-3432) is isolated and cloned into the SmaI restriction site in the low copy yeast shuttle vector pRS416 [ATCC #87521] to create plasmid pROS-911 (selections: URA for yeast and Amp for bacteria). The plasmid is propagated in the SURE bacterial strain (Stratagene, La Jolla, Calif.) under Amp selection.

AAV Rep 52 and VP3 Plasmid: For expression of AAV2 VP3, the AAV VP3 coding region was generated from pIM-45 by PCR using Platinum® PCR SuperMix (Invitrogen, Carlsbad, Calif.) and gene-specific oligonucleotide primers (200 nM final concentration) with the following sequences:

(SEQ ID NO: 14)
5' CGGGATCCAAAAAAAATGGCTACAGGCAGTGGCGC 3'
(35-mer)

The underlined nucleotides of SEQ ID NO:14 indicate a BamHI restriction site.

5' CCCAAGCTTTTACAGATTACGAGTCAGG 3' (SEQ ID NO: 15)
(28-mer)

The underlined nucleotides of SEQ ID NO:15 indicate a HindIII restriction site.

The cycling parameters are as follows:

| Cycle   | Step | Description          | Set Point | Time       |
|---------|------|----------------------|-----------|------------|
| 1 (1x)  | 1    | Initial Denaturation | 94° C.    | 3 minutes  |
| 2 (35x) | 1    | Denature             | 94° C.    | 30 seconds |
|         | 2    | Anneal               | 57° C.    | 30 seconds |
|         | 3    | Extend               | 72° C.    | 2 minutes  |
| 3 (1x)  | 1    | Final Extension      | 72° C.    | 5 minutes  |

The 1603 bp PCR product was digested with BamHI and HindIII and then cloned into BamHI-HindIII digested pESC-LEU (Stratagene, La Jolla, Calif.) using the Quick Ligation™ Kit (New England BioLabs, Beverly, Mass.) to create pROS-920 and sequenced. Expression of VP3 is under the control of the GAL1 promoter. The plasmid is propagated in the DH5-α bacterial strain under Amp selection. For expression of AAV2 Rep52, the AAV Rep52 coding region was generated from pIM-45 by PCR using Platinum® PCR SuperMix (Invitrogen, Carlsbad, Calif.) and gene-specific oligonucleotide primers (200 nM final concentration) with the following sequences:

(SEQ ID NO: 16)
5' ATAAGAATGCGGCCGCAAAAAAAATGGAGCTGGTCGGGTGG 3'
(41-mer)

The underlined nucleotides of SEQ ID NO:16 indicate a NotI restriction site.

(SEQ ID NO: 17)
5' CCTTAATTAATTATTGTTCAAAGATGCAG 3'
(29-mer)

The underlined nucleotides of SEQ ID NO:17 indicate a PacI restriction site.

The cycling parameters are as follows:

| Cycle   | Step | Description          | Set Point | Time       |
|---------|------|----------------------|-----------|------------|
| 1 (1x)  | 1    | Initial Denaturation | 94° C.    | 3 minutes  |
| 2 (35x) | 1    | Denature             | 94° C.    | 30 seconds |
|         | 2    | Anneal               | 57° C.    | 30 seconds |
|         | 3    | Extend               | 72° C.    | 2 minutes  |
| 3 (1x)  | 1    | Final Extension      | 72° C.    | 5 minutes  |

The 1195 bp PCR product was digested with NotI and PacI and then cloned into NotI-PacI digested pROS-920 to create pROS-921 and sequenced. Expression of Rep52 is under the control of the GAL10 promoter. Thus, pROS-921 (selections: LEU for yeast and Amp for bacteria) expresses both AAV VP3 and Rep52 under the control of the galactose-inducible GAL1 and GAL10 promoters on a high copy plasmid. The plasmid is propagated in the DH5-α bacterial strain under Amp selection.

AAV VP1, VP2, and Rep 78 Plasmid: pRS-414 [ATCC #87519] was digested with ScaI and NaeI. The 2589 bp fragment containing the low copy number origin ARSH4, CEN6, and TRP1 elements (position 3762-1566) was isolated. pESC-TRP (Stratagene, La Jolla, Calif.) was digested with ScaI and NaeI to remove the high copy number 2-micron origin and TRP1 elements (position 1569-4677). The 2589 bp ScaI-NaeI origin fragment from pRS-414 was then ligated to the 3108 bp ScaI-NaeI fragment of pESC-TRP using the Quick Ligation™ Kit (New England BioLabs, Beverly, Mass.) to create pROS-711 (selections: TRP1 for yeast and Amp for bacteria), a low copy number plasmid with both the GAL1 and GAL10 promoters. The plasmid is propagated in the DH5-α strain under Amp selection.

For expression of AAV2 VP1, the AAV VP1 coding region was generated from pIM-45 by PCR using Platinum® PCR SuperMix (Invitrogen, Carlsbad, Calif.) and gene-specific oligonucleotide primers (200 nM final concentration) with the following sequences:

(SEQ ID NO: 18)
5' CGGGATCCAAAAAAAATGGCTGCCGATGGTTATC 3'
(34-mer)

The underlined nucleotides of SEQ ID NO:18 indicate a BamHI restriction site.

5' CTAGCTAGCTTACAGATTACGAGTCAGG 3' (SEQ ID NO: 19)
(28-mer)

The underlined nucleotides of SEQ ID NO:19 indicate a NheI restriction site.

The cycling parameters are as follows:

| Cycle | Step | Description | Set Point | Time |
|---|---|---|---|---|
| 1 (1x) | 1 | Initial Denaturation | 94° C. | 3 minutes |
| 2 (35x) | 1 | Denature | 94° C. | 30 seconds |
|  | 2 | Anneal | 57° C. | 30 seconds |
|  | 3 | Extend | 72° C. | 2 minutes |
| 3 (1x) | 1 | Final Extension | 72° C. | 5 minutes |

The 2209 bp PCR product was digested with BamHI and NheI then cloned into BamHI-NheI digested pROS-711 to create pROS-912 and sequenced. Expression of VP1 is under the control of the GAL1 promoter. The plasmid is propagated in the DH5-α strain under Amp selection.

For expression of AAV2 VP2, the AAV VP2 coding region was generated from pIM-45 by PCR using Platinum® PCR SuperMix (Invitrogen, Carlsbad, Calif.) and gene-specific oligonucleotide primers (200 nM final concentration) with the following sequences:

(SEQ ID NO: 20)
5' ATAAGAATGCGGCCGCAAAAAAAATGGCTCCGGGAAAAAAGAGGC 3'
(45-mer).

The underlined nucleotides of SEQ ID NO:20 indicate a NotI restriction site.

(SEQ ID NO: 21)
5' CCTTAATTAATTACAGATTACGAGTCAGG 3'
(29-mer)

The underlined nucleotides of SEQ ID NO:21 indicate a PacI restriction site.

The cycling parameters are as follows:

| Cycle | Step | Description | Set Point | Time |
|---|---|---|---|---|
| 1 (1x) | 1 | Initial Denaturation | 94° C. | 3 minutes |
| 2 (35x) | 1 | Denature | 94° C. | 30 seconds |
|  | 2 | Anneal | 57° C. | 30 seconds |
|  | 3 | Extend | 72° C. | 2 minutes |
| 3 (1x) | 1 | Final Extension | 72° C. | 5 minutes |

The 1798 bp PCR product was digested with NotI and PacI and then cloned into NotI-PacI digested pROS-912 to create pROS-913 and sequenced. Expression of VP2 is under the control of the GAL10 promoter. Thus, pROS-913 (selections: TRP for yeast and Amp for bacteria) expresses both AAV VP1 and VP2 under the control of the galactose-inducible GAL1 and GAL10 promoters on a low copy plasmid. The plasmid is propagated in the DH5-α bacterial strain under Amp selection.

For expression of AAV2 Rep78, the AAV Rep78 coding region was generated from pIM-45 by PCR using Platinum® PCR SuperMix (Invitrogen, Carlsbad, Calif.) and gene-specific oligonucleotide primers (200 nM final concentration) with the following sequences:

(SEQ ID NO: 22)
5' ATAAGAATGCGGCCGCAAAAAAAATGCCGGGGTTTTACGAG 3'
(41-mer)

The underlined nucleotides of SEQ ID NO:22 indicate a NotI restriction site.

(SEQ ID NO: 17)
5' CCTTAATTAATTATTGTTCAAAGATGCAG 3'
(29-mer)

The underlined nucleotides of SEQ ID NO:17 indicate a PacI restriction site.

The cycling parameters are as follows:

| Cycle | Step | Description | Set Point | Time |
|---|---|---|---|---|
| 1 (1x) | 1 | Initial Denaturation | 94° C. | 3 minutes |
| 2 (35x) | 1 | Denature | 94° C. | 30 seconds |
|  | 2 | Anneal | 57° C. | 30 seconds |
|  | 3 | Extend | 72° C. | 2 minutes |
| 3 (1x) | 1 | Final Extension | 72° C. | 5 minutes |

The 1867 bp PCR product was digested with NotI and PacI and then cloned into Not1-PacI digested pESC-TRP (Stratagene, La Jolla, Calif.) to create pROS-922 and sequenced. Expression of Rep78 is under the control of the GAL10 promoter. The plasmid is propagated in the DH5-α bacterial strain under Amp selection.

pROS-922 was digested with SapI and NaeI and blunt-ended using Klenow fragment. The fragment containing the AAV Rep78 coding region was then cloned into the NaeI site of pROS-913 to create pROS-914 (selections: TRP for yeast and Amp for bacteria), a low copy number plasmid with AAV VP1 under control of the GAL1 promoter, VP2 under control of the GAL10 promoter, and Rep78 under control of the GAL10 promoter. The plasmid is propagated in the DH5-α bacterial strain under Amp selection.

Example 6 rAAV Virion Production in Yeast

Yeast Strains. Yeast cells used in methods of the invention may be haploid or diploid cells. In a particular method of the invention, an rAAV vector plasmid pROS-910 or pROS-911 is transformed using electroporation into yeast strain BJ2168 [ATCC 208277] plated and selected on uracil-deficient agar media; the subsequent strain is called YRS-1. The plasmid pROS-921 expressing AAV VP3 and Rep 52 proteins is transformed into YRS-1 and plated and selected on uracil and leucine-deficient agar media to create strain YRS-2. Strain YRS-2 is transformed with pROS-914, expressing AAV capsid proteins VP 1 and VP2, and Rep78, and plated and selected on uracil, leucine, and tryptophan-deficient agar media to create strain YRS-3.

To screen colonies for AAV protein expression and rAAV production, YRS-3 colonies are grown on SD-dropout-LEU-TRP-URA plates (glucose) at 30° C. overnight and inoculated into 10 ml of SG-dropout-LEU-TRP-URA media (galactose), cultured for 16 hours, and samples are taken every 2 hours. Cells are harvested by centrifugation at 2000 g for 5 min at 4° C. and frozen at −70° C. Whole cell lysates are made in lysis buffer using glass beads, and separated on a 10% SDS-PAGE gel, transferred to nitrocellulose and probed with anti-Rep (295.5, Progen, Brisbane, Australia) and anti-Cap (B1, Progen, Brisbane, Australia) antibodies. Detection is carried out using anti-mouse HRP conjugated monoclonal antibody and Pierce SuperSignal reagent (Pierce, Rockford, Ill.). In addition, replication of the rAAV-UF-5 vector genome is evaluated by isolating vector DNA by the method of Hirt (J. Mol. Biol. 26:365, 1967) and separating on a 1% agarose gel followed by Southern blotting with a GFP fragment probe. Infectious virions are detected by infecting 293 tissue culture cells with yeast lysates that are treated with chloroform and scoring for GFP expression.

rAAV Virion Production. Large-scale culturing of yeast and expression of proteins under galactose control is carried out according to Burgers, Methods 18:349, 1999. Yeast strain YRS-3 is grown for 2-3 days in 100 ml of uracil, leucine, and tryptophan selective SCGL medium at 30° C. until saturation and inoculated into 1200 ml of the same medium in a 4-liter flask and grown overnight. An equal volume of YPGLA is then added to the overnight culture. The culture is equally divided between two flasks and grown at 30° C. for 3 h. Solid galactose (26 g per flask, 2% final) is then added to the cultures and shaking continued for another 4 h. The cells are harvested by centrifugation at 1500 g for 5 min at 4° C. The yeast is stored frozen at −70° C.

rAAV Virion Purification. Yeast is resuspended in lysis buffer (20 mM Tris-Cl pH=8, 150 mM NaCl, 0.5% deoxychloate), and lysed using glass beads. The lysate is treated with Benzonase (Sigma, St. Louis, Mo.) and centrifuged at 4000 g and the supernatant is chromatographed on Streamline HE column (Pharmacia), Phenyl Sepharose, and POROS HE (Potter et al., Methods Enzymol 346:413-30, 2002).

rAAV Virion Performance. The purified rAAV vectors are used to infect 293 cells in culture or injecting into mouse skeletal muscle to assess their infectivity by scoring for cells expressing GFP.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of producing recombinant AAV virions comprising:
providing a first vector comprising an exogenous nucleic acid interposed between a first AAV terminal repeat and a second AAV terminal repeat, a promoter operably linked to the exogenous nucleic acid, and a yeast origin of replication;
providing a second vector comprising a first AAV rep gene, a first AAV cap gene, and a yeast origin of replication wherein the rep gene and the cap gene are operably linked to at least one promoter;
introducing the first vector and the second vector into a yeast cell; and
culturing the yeast cell under conditions such that recombinant AAV virions are produced.

2. The method of claim 1, further comprising collecting the recombinant AAV virions from the culture.

3. The method of claim 1, wherein the first and the second AAV terminal repeats are serotype 2.

4. The method of claim 1, wherein the first AAV rep gene encodes Rep78, and the first AAV cap gene encodes VP 1.

5. The method of claim 4, wherein the at least second vector further comprises a second AAV cap gene which is operably linked to an expression control sequence.

6. The method of claim 5, wherein the second AAV cap gene encodes VP2.

7. The method of claim 5, wherein the first AAV cap gene is operatively linked to both a GAL1 promoter and a CYC1 transcription termination region, the at least second AAV cap gene is operatively linked to both a GAL10 promoter and a ADH1 transcription termination region, the first AAV rep gene is operatively linked to both a GAL10 promoter and a ADH1 transcription termination region, and wherein the at second vector further comprises an ARS4 sequence, a CEN6 sequence, and a TRP1 selectable marker.

8. The method of claim 1, further comprising introducing into the yeast cell a third vector comprising a second AAV rep gene, a third AAV cap gene, and a yeast origin of replication wherein the rep gene and the cap gene are operably linked to at least one promoter.

9. The method of claim 8, wherein the second AAV rep gene encodes Rep52 and the at least third AAV cap gene encodes VP3.

10. The method of claim 9, wherein the third AAV cap gene is operatively linked to both a GAL1 promoter and a CYC1 transcription termination region, and the second AAV rep gene is operatively linked to both a GAL10 promoter and a ADH1 transcription termination region, and wherein the third vector comprises a LEU2 selectable marker and wherein the yeast origin of replication is a 2 micron origin of replication.

11. The method of claim 8, wherein each of the first, second, and third vectors further comprises a yeast selectable marker selected from the group consisting of: TRP1, HIS3, URA3, LYS2 or LEU2, wherein the first, second, and third vectors comprise different ones of said selectable markers.

12. The method of claim 8, wherein each of the first, second and third vectors each comprise a yeast origin of replication selected from the group consisting of: a 2 micron yeast origin of replication, and an autonomously replicating sequence comprising CEN6 and ARS4.

13. The method of claim 1, wherein the exogenous nucleic acid is a reporter gene or a therapeutic gene.

14. The method of claim 13, wherein the reporter gene encodes green fluorescent protein.

15. The method of claim 13, wherein the therapeutic gene encodes a protein selected from the group consisting of: an alpha-one antitrypsin, a clotting factor IX, a clotting factor VIII, a clotting factor VII, a dystrophin, an α-sarcoglycan, αβ-sarcoglycan, an δ-sarcoglycan, a ε-sarcoglycan, a tyrosine hydroxylase, an aromatic acid decarboxylase, a GTP cyclohydrolase I, an erythropoietin, an aspartoacylase (ASPA), a Nerve growth factor (NGF), a lysosomal beta-glucuronidase (GUSB), an insulin, an alpha-synuclein, a basic fibroblast growth factor (FGF-2), an IGF 1, an alpha-galactosidase A (alpha-gal A), a neurotrophin-3, a Neuroglobin (Ngb), an angiogenic protein a vascular endothelial growth factor (VEGF165, an anti-angiogenic protein, a cytokine, an interferon, IFN-α, IFN-β, IFN-γ, an interleukin, a GM-CSF (granulocyte-macrophage colony-stimulating factor), a M-CSF (macrophage colony-stimulating factor), a tumor necrosis factor, a growth factor, a TGF-β. (transforming growth factor-β.), an IL-10, an IL-13, an IL-4, a PDGF (platelet-derived growth factor), a neurotrophic factor, a CNTF (ciliary Neurotrophic factor), a brain-derived neurotrophic factor (BDNF), and GDNF (glial cell line derived neurotrophic factor) protein.

16. The method of claim 1, wherein the promoter is a cytomegalovirus promoter.

* * * * *